(12) United States Patent
Yatagai et al.

(10) Patent No.: US 7,592,480 B2
(45) Date of Patent: Sep. 22, 2009

(54) PROCESS FOR PRODUCING OPTICALLY ACTIVE CARBOXYLIC ACID

(75) Inventors: Masanobu Yatagai, Kawasaki (JP);
Masafumi Minomura, Kawasaki (JP);
Shigekatsu Tsuchiya, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 242 days.

(21) Appl. No.: 10/934,724

(22) Filed: Sep. 7, 2004

(65) Prior Publication Data

US 2005/0065368 A1 Mar. 24, 2005

Related U.S. Application Data

(63) Continuation of application No. PCT/JP03/02455, filed on Mar. 4, 2003.

(30) Foreign Application Priority Data

Mar. 6, 2002 (JP) ............... 2002-060560

(51) Int. Cl.
*C07B 57/00* (2006.01)
*C07C 61/04* (2006.01)
(52) U.S. Cl. ..................... 562/401; 562/506
(58) Field of Classification Search ........... 562/401, 562/506
See application file for complete search history.

(56) References Cited

U.S. PATENT DOCUMENTS 5,166,417 A 11/1992 Meul
5,278,337 A 1/1994 Manimaran et al.

FOREIGN PATENT DOCUMENTS

| EP | 0 093 511 | | 11/1983 |
| GB | 1260847 | * | 1/1972 |
| WO | 02/22543 A1 | | 3/2002 |

OTHER PUBLICATIONS

Martak et al, L/L equilibria of dimethylcyclopropanecarboxylicacid in water-solvent systems with trioctylamine as an extractant, 2000, 54(6b), p. 413-422.*
Catalog Handbook of Fine Chemicals Aldrich, 1998-1999, p. 165 and p. 1087.*

* cited by examiner

*Primary Examiner*—Taylor Victor Oh
(74) *Attorney, Agent, or Firm*—Suzanne M. Hopkins; Ari G. Zytcer; Charles D. Niebylski

(57) ABSTRACT

The invention provides a process for producing optically active 2,2-dimethylcyclopropanecarboxylic acid by reacting an optical isomer mixture of 2,2-dimethylcyclopropanecarboxylic acid with an optically inactive amine to form (precipitate, crystallize or the like) an ammonium salt of optically active 2,2-dimethylcyclopropanecarboxylic acid, for example, optically active (S)-(+)-2,2-dimethylcyclopropanecarboxylic acid. The production (optical resolution, separation of an optically active substance, purification of an optically active substance or the like) of optically active 2,2-dimethylcyclopropanecarboxylic acid which is important as an intermediate for production of agricultural chemicals, medications and the like can easily be conducted at low cost. Further, the invention provides an intermediate therefor (an ammonium salt of optically active 2,2-dimethylcyclopropanecarboxylic acid, especially preferably an ammonium salt of optically active (S)-(+)-2,2-dimethylcyclopropanecarboxylic acid, or the like), and an optical resolution agent (optically inactive amine) for separation of optically active 2,2-dimethylcyclopropanecarboxylic acid.

10 Claims, No Drawings

PROCESS FOR PRODUCING OPTICALLY ACTIVE CARBOXYLIC ACID

CROSS-REFERENCE TO RELATED APPLICATIONS

The present application is a continuation of International application PCT/JP03/02455, filed on Mar. 4, 2003, and claims priority to Japanese application No. 2002-060560, filed on Mar. 6, 2002, which are hereby incorporated by reference in their entirety.

TECHNICAL FIELD

The present invention relates to a novel process for producing optically active carboxylic acid, specifically optically active 2,2-dimethylcyclopropanecarboxylic acid, especially its S-isomer. More specifically, it relates to a process for producing optically active 2,2-dimethylcyclopropanecarboxylic acid which is important as an intermediate of agricultural chemicals, medications and the like from 2,2-dimethylcyclopropanecarboxylic acid including its optical isomer mixture (a racemic modification or an optically impure substance) by formation (precipitation, crystallization or the like) of an ammonium salt with an optically inactive amine, a novel ammonium salt being a novel intermediate therefor, an optically inactive amine being an optical resolution agent used therefor, and the like.

BACKGROUND ART

Optically active 2,2-dimethylcyclopropanecarboxylic acid, especially its optically active substance (S-isomer or the like) is a compound which is quite useful as an intermediate of agricultural chemicals such as an insecticide (refer to a specification of British Patent No. 1,260,847) or medications (refer to Kagaku to Seibutsu (Chemistry and Biology), 19, 204 (1981), EP 0,048,301 and the like). Especially, the S-isomer ((S)-(+)-2,2-dimethylcyclopropanecarboxylic acid) is a compound represented by the following formula (2), and this is an optically active substance which is more useful as a production intermediate.

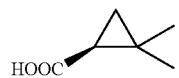

(2)

With respect to a method for optical resolution of optically active 2,2-dimethylcyclopropanecarboxylic acid, there have been to date several reports. For example, a method for optical resolution by crystallization after derivatization into a diastereomer ester with a chiral alcohol or a diastereomer salt with a chiral amine (refer to a specification of British Patent No. 1,260,847, JP-A-60-25956, JP-A-60-56936 and the like) is known. For the diastereomer method, the improvement in optical purity or yield has been required in comparison to an asymmetric synthesis method.

For example, according to a method for optical resolution with phenylethylamine, a yield and an optical purity are both insufficient. According to a method using an ester with 1-menthol (refer to JP-A-60-25956), a satisfactory optical purity is provided, but the method is relatively troublesome because derivatization into an acid chloride or the like is conducted.

Assuming that a desired optical purity is attained by the optical resolution method, an optical resolution agent is expensive. Accordingly, when production was estimated on a large scale, there was a problem that recovery of the optical resolution agent had to be taken into consideration.

Under these circumstances, further improvements have been required for the optical resolution or optical purification method.

DISCLOSURE OF THE INVENTION

1. Problems that the Invention is to Solve

With respect to a process in which optically active 2,2-dimethylcyclopropanecarboxylic acid which is important as an intermediate for production of agricultural chemicals, medications and the like is separated and purified (produced) from 2,2-dimethylcyclopropanecarboxylic acid including an optical isomer mixture (racemic modification or an optically impure substance) of 2,2-dimethylcyclopropanecarboxylic acid, the invention aims to develop a process by which resolution and purification (production) of the desired optically active substance can easily be performed at low cost.

2. Means for Solving the Problems

The present inventors have assiduously conducted investigations to solve the foregoing problems, and have consequently found that when optically active 2,2-dimethylcyclopropanecarboxylic acid is contained in an optical isomer mixture of optically active 2,2-dimethylcyclopropanecarboxylic acid in an equimolar amount or more relative to the other isomer and the optical isomer mixture is brought into contact with an optically inactive amine, the amine is preferentially reacted with the optically active 2,2-dimethylcyclopropanecarboxylic acid to easily form its ammonium salt (for example, when optically active (S)-(+)-2,2-dimethylcyclopropanecarboxylic acid is contained in an optical isomer mixture of optically active 2,2-dimethylcyclopropanecarboxylic acid in an equimolar amount or more relative to the other isomer, the amine is preferentially reacted with optically active (S)-(+)-2,2-dimethylcyclopropanecarboxylic acid to easily form its ammonium salt), so that the amine is excellent as an optical resolution agent for optically active 2,2-dimethylcyclopropanecarboxylic acid. Further, it has been found that the thus-formed (for example, precipitated or crystallized) salt is separated and subjected to a desalting step (a step of forming a free compound from a salt) so that an optically active free compound is easily obtained with a high optical purity in high yield, and that since the amine (including ammonia) is inexpensive, it is industrially quite advantageous as an optical resolution agent. These various findings have led to the completion of the invention.

That is, the invention resides in a process for producing optically active 2,2-dimethylcyclopropanecarboxylic acid (which may be in the form of an ammonium salt), characterized by comprising reacting an optical isomer mixture of 2,2-dimethylcyclopropanecarboxylic acid with an optically inactive amine to form an ammonium salt of optically active 2,2-dimethylcyclopropanecarboxylic acid (hereinafter also referred to as an "invention process for producing optically active 2,2-dimethylcyclopropanecarboxylic acid").

In the invention process for producing optically active 2,2-dimethylcyclopropanecarboxylic acid, when optically active (S)-(+)-2,2-dimethylcyclopropanecarboxylic acid is contained in the optical isomer mixture in an equimolar amount or more relative to the other isomer, optically active (S)-(+)-2,2-dimethylcyclopropanecarboxylic acid can be produced in higher yield with a high optical purity. When at least an R-isomer of optically active 2,2-dimethylcyclopropanecarboxylic acid ((R)-(−)-2,2-dimethylcyclopropanecarboxylic acid) is contained in the optical isomer mixture as an impurity, this can easily be separated and removed because of a small amount (impurity amount).

When the optical isomer mixture is a racemic modification of 2,2-dimethylcyclopropanecarboxylic acid, it can also be reacted with the optically inactive amine to form an ammonium salt of optically active 2,2-dimethylcyclopropanecarboxylic acid. Preferably, the formation of the ammonium salt can easily be conducted using, as a seed crystal, a desired ammonium salt of optically active 2,2-dimethylcyclopropanecarboxylic acid or a high-purity ammonium salt of optically active 2,2-dimethylcyclopropanecarboxylic acid. Here, when the optical purity of the resulting ammonium salt is low, an optically active substance with a high optical purity can be produced by further repeating this invention. A process for producing optically active 2,2-dimethylcyclopropanecarboxylic acid with such a low optical purity is also included in the invention.

Meanwhile, as the optically inactive amine, a primary to tertiary amine represented by the following general formula (1) can be used.

wherein $R_1$, $R_2$ and $R_3$ are independent, and each represents (a) a saturated or unsaturated, linear or branched hydrocarbon group with from 1 to 8 carbon atoms which may have an alicyclic or aromatic substituent;

(b) a heterocyclic hydrocarbon group containing an oxygen atom and/or a nitrogen atom, which may have a saturated or unsaturated, linear or branched hydrocarbon group;

(c) an alicyclic hydrocarbon group with from 3 to 8 carbon atoms;

(d) an aromatic hydrocarbon group which may have a saturated or unsaturated, linear or branched hydrocarbon group; or (e) a hydrogen atom (provided ammonia is also included).

In the invention, ammonia is also included in the "optically inactive amine".

When at least one, preferably any one of t-butylamine, cyclohexylamine, diisopropylamine, dicyclohexylamine and benzylamine is used as the optically inactive amine, the optically active 2,2-dimethylcyclopropanecarboxylic acid can be produced in high yield with a high optical purity.

The invention process for producing optically active 2,2-dimethylcyclopropanecarboxylic acid can include a step of subjecting the ammonium salt of optically active 2,2-dimethylcyclopropanecarboxylic acid to a desalting step (a step of converting a salt to a free compound) to form a free compound of optically active 2,2-dimethylcyclopropanecarboxylic acid.

In the invention process for producing optically active 2,2-dimethylcyclopropanecarboxylic acid, when the reaction of the ammonium salt formation is conducted in a solution appropriate for its formation or precipitation, the ammonium salt of optically active 2,2-dimethylcyclopropanecarboxylic acid is easily separated and purified.

Accordingly, the invention process for producing optically active 2,2-dimethylcyclopropanecarboxylic acid can include a step of obtaining a precipitated ammonium salt of optically active 2,2-dimethylcyclopropanecarboxylic acid, for example, an ammonium salt of optically active (S)-(+)-2,2-dimethylcyclopropanecarboxylic acid, a step of subjecting the resulting ammonium salt to a desalting step, namely a step of converting a salt to a free compound to obtain optically active 2,2-dimethylcyclopropanecarboxylic acid, for example, an S-isomer (free compound) of optically active 2,2-dimethylcyclopropanecarboxylic acid, a step of separating the other optical isomer of 2,2-dimethylcyclopropanecarboxylic acid in the solution, for example, an R-isomer of optically active 2,2-dimethylcyclopropanecarboxylic acid, and the like.

In another embodiment, the invention resides in optically active 2,2-dimethylcyclopropanecarboxylic acid, for example, its S-isomer, characterized by being in the form of an ammonium salt with an optically inactive amine (hereinafter also referred to as an "invention ammonium salt"). The optically inactive amine is as described earlier.

In still another embodiment, the invention resides in an optical resolution agent for separation of optically active 2,2-dimethylcyclopropanecarboxylic acid by formation of an ammonium salt, characterized by containing an optically inactive amine. The optically inactive amine is as described earlier.

In the other embodiment, the invention resides in a method for optical purification of optically active 2,2-dimethylcyclopropanecarboxylic acid, characterized by comprising reacting an optical isomer mixture of 2,2-dimethylcyclopropanecarboxylic acid with an optically inactive amine to form an ammonium salt of optically active 2,2-dimethylcyclopropanecarboxylic acid (hereinafter also referred to as an "invention method for optical purification of optically active 2,2-dimethylcyclopropanecarboxylic acid).

In the invention method for optical purification of optically active 2,2-dimethylcyclopropanecarboxylic acid, for example, when optically active (S)-(+)-2,2-dimethylcyclopropanecarboxylic acid is contained in the optical isomer mixture in an equimolar amount or more relative to the other isomer, the optically active (S)-(+)-2,2-dimethylcyclopropanecarboxylic acid can be separated and purified in higher yield with a high optical purity. When the optical isomer mixture contains at least an R-isomer of optically active 2,2-dimethylcyclopropanecarboxylic acid as an impurity, it can easily be separated and removed in the same manner. The optically inactive amine is as described earlier.

In the other embodiment, the invention resides in a process for producing optically active 2,2-dimethylcyclopropanecarboxylic acid, characterized by comprising subjecting optically active 2,2-dimethylcyclopropanecarboxylic acid in the form of an ammonium salt with an optically inactive amine to a desalting step to form its free compound (hereinafter also referred to as an "invention process for producing a free compound of optically active 2,2-dimethylcyclopropanecarboxylic acid") The optically inactive amine is as described earlier.

When the ammonium salt or the free compound of optically active 2,2-dimethylcyclopropanecarboxylic acid is produced in the invention, especially, optically active 2,2-dimethylcyclopropanecarboxylic acid (or its ammonium salt), for example, optically active (S)-(+)-2,2-dimethylcyclopropanecarboxylic acid (or its ammonium salt), having an optical purity of, preferably at least 92% e.e. (enantiomer excess) (92% e.e. or more), more preferably at least 95% e.e., further preferably at least 99% e.e. can be produced.

Production of optically active 2,2-dimethylcyclopropanecarboxylic acid (or its ammonium salt) containing other isomers is naturally included in the invention, though the optical purity might be low.

Mode for Carrying Out the Invention

Embodiments of the invention are described below.

The invention includes the process for producing a desired optically active substance by formation of a salt of an optically active substance with an optically inactive amine, separation and, as required, desalting (formation of a free compound from a salt). The invention process for producing optically active 2,2-dimethylcyclopropanecarboxylic acid and the invention method for optical purification of optically active 2,2-dimethylcyclopropanecarboxylic acid are described mainly in case of containing optically active (S)-(+)-2,2-dimethylcyclopropanecarboxylic acid in an optical isomer mixture of 2,2-dimethylcyclopropanecarboxylic acid in an equimolar amount or more in particular. However, the invention is not limited thereto. For example, when optically active (R)-(−)-2,2-dimethylcyclopropanecarboxylic acid is contained in the optical isomer mixture in an equimolar amount or more, optically active (R)-(−)-2,2-dimethylcyclopropanecarboxylic acid can also be produced easily in higher yield with a high optical purity.

Invention Process for Producing Optically Active 2,2-dimethylcyclopropanecarboxylic acid)

The invention process for producing optically active 2,2-dimethylcyclopropanecarboxylic acid is described.

The starting material used in the invention can be a mixture containing optically active 2,2-dimethylcyclopropanecarboxylic acid. For example, an optically active 2,2-dimethylcyclopropanecarboxylic acid in which optically active (S)-(+)-2,2-dimethylcyclopropanecarboxylic acid and at least its optical isomer (R-isomer) as an impurity are contained in an optical isomer mixture of 2,2-dimethylcyclopropanecarboxylic acid, or a racemic modification of 2,2-dimethylcyclopropanecarboxylic acid are used.

A large number of synthesis examples have been reported on 2,2-dimethylcyclopropanecarboxylic acid in the form of the racemic modification, and it can easily be synthesized (refer to E. R. Nelson, J. Am. Chem. Soc., 79, 3467 (1957) and the like).

The optically inactive amine used in the invention is not particularly limited, and a commercially available product can be procured and used. The optically inactive amine which is specifically selected is preferably the primary to tertiary amine represented by the following general formula (1) as described earlier, and it is more preferable to select a primary or secondary amine represented by the following general formula (3);

$$R_2 \underset{\underset{R_1}{|}}{\overset{}{N}} R_3 \quad (1)$$

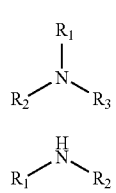

(3)

In the formulas, $R_1$, $R_2$ and $R_3$ are independent, and each represents (a) a saturated or unsaturated, linear or branched hydrocarbon group with from 1 to 8 carbon atoms which may have an alicyclic or aromatic substituent;

(b) a heterocyclic hydrocarbon group containing an oxygen atom and/or a nitrogen atom, which may have a saturated or unsaturated, linear or branched hydrocarbon group;

(c) an alicyclic hydrocarbon group with from 3 to 8 carbon atoms;

(d) an aromatic hydrocarbon group which may have a saturated or unsaturated, linear or branched hydrocarbon group; or (e) a hydrogen atom, provided ammonia is also included in the optically inactive amine as described above.

The saturated or unsaturated, linear or branched hydrocarbon group with from 1 to 8 carbon atoms is a group with from 1 to 8 carbon atoms. Examples of the saturated hydrocarbon group include a methyl group, an ethyl group, a propyl group, a butyl group (t-butyl group or the like) and the like. Examples of the unsaturated hydrocarbon group include a vinyl group, an allyl group and the like. These hydrocarbon groups are linear or branched. These hydrocarbon groups may have further a substituent(s), examples thereof including alicyclic hydrocarbon groups such as cyclopropyl, cyclobutyl, cyclopentyl and cyclohexyl and aromatic hydrocarbon groups such as phenyl. Meanwhile, examples of the alicyclic hydrocarbon group with from 3 to 8 carbon atoms include cyclopropyl, cyclobutyl, cyclopentyl, cyclohexyl and the like. Examples of the aromatic hydrocarbon group, which may have a saturated or unsaturated, linear or branched hydrocarbon group(s), include phenyl, methylphenyl, ethylphenyl and the like. With respect to the heterocyclic hydrocarbon group containing an oxygen atom(s) and/or a nitrogen atom(s), which may have saturated or unsaturated, linear or branched hydrocarbon group(s), examples of the group can include furyl, pyridyl, furylmethyl, pyridylmethyl, methylpyridyl, methylfuryl and the like.

More preferably, at least one, especially any one of t-butylamine, cyclohexylamine, diisopropylamine, dicyclohexylamine and benzylamine is selected. These can be used either singly or in combination of two or more.

With respect to the amount of the optically inactive amine (optical resolution agent) used in the invention, in order to form a desired ammonium salt, the amine can be used at a molar ratio of, preferably 1:0.1 to 5, more preferably 1:0.8 to 3, further preferably 1:0.8 to 1.2 relative to optically active 2,2-dimethylcyclopropanecarboxylic acid present in a starting material.

The formation of the ammonium salt in the invention can be conducted in an appropriate solution. As a usable solvent, it is advisable to select a solvent (including a mixture of plural solvents) which can fully dissolve both of the compounds and is not reacted with the substances constituting the ammonium salt. Preferable examples thereof include organic solvents such as ethyl acetate, isobutyl acetate, butyl acetate, toluene, methylene chloride, chloroform and an alcohol having from 1 to 4 carbon atoms, water, and mixed solvents thereof, which is, more preferably, a homogeneous solvent. Further preferably, a solvent which provides a formed salt with a predetermined solubility and from which the salt can be precipitated or crystallized (recrystallized or the like) is used of course, it is also possible to select different solvents in salt formation, salt recrystallization and salt reprecipitation.

The invention can include a step of obtaining a precipitated ammonium salt of optically active 2,2-dimethylcyclopropanecarboxylic acid, for example, an ammonium salt of optically active (S)-(+)-2,2-dimethylcyclopropanecarboxylic acid, a step of subjecting the resulting ammonium salt to a desalting step (a step of forming a free compound from a salt) to obtain optically active 2,2-dimethylcyclopropanecarboxylic acid, for example, an S-isomer of optically active 2,2-dimethylcyclopropanecarboxylic acid, a step of separating other optical isomers of 2,2-dimethylcyclopropanecarboxylic acid, for example, an R-isomer of optically active 2,2-dimethylcyclopropanecarboxylic acid in the solution, and the like.

That is, when the desired compound to be resolved or separated is optically active (S)-(+)-2,2-dimethylcyclopropanecarboxylic acid, a desired ammonium salt is formed (precipitated, crystallized or the like) using the optically inactive amine as the optical resolution agent, and this is separated to obtain the desired compound. Further, the resulting ammonium salt is subjected to a desalting step, whereby an S-isomer (free compound) of optically active 2,2-dimethylcyclopropanecarboxylic acid can be obtained with a high optical purity, preferably at least 92% e.e., more preferably at least 95% e.e., further preferably at least 99% e.e. Meanwhile, it is possible that, for example, an ammonium salt of optically active (S)-(+)-2,2-dimethylcyclopropanecarboxylic acid is preferentially formed (precipitated, crystallized or the like) using the optically inactive amine, and (R)-(−)-2,2-dimethylcyclopropanecarboxylic acid is resolved or separated from the solution (mother liquor) with the ammonium salt separated.

It is advisable that for forming a free compound (enantiomer) of optically active 2,2-dimethylcyclopropanecarboxylic acid from the separated ammonium salt, the salt is subjected to a desalting step. For example, it can be attained by contact with a strong acid (hydrochloric acid, sulfuric acid or the like). A step of treatment with a strong acid can be performed in a water medium. The use amount of water can be selected such that the thus-formed salt of the strong acid and the amine is fully dissolved in water.

A major part of the thus-obtained free compound of optically active 2,2-dimethylcyclopropanecarboxylic acid is separated as an oil, and a part thereof is dissolved in an aqueous phase. When the part dissolved in the aqueous phase is separated, it can be extracted and separated with, for example, an organic solvent.

Preferable examples of the organic solvent can include hydrocarbons having from 5 to 8 carbon atoms, such as pentane, hexane, heptane, octane, cyclohexane and methylcyclohexane, esters such as ethyl acetate, halogen-based solvents such as methylene chloride, and the like. Of these, ethyl acetate can be used especially preferably. After the extraction, such an extraction solvent can easily be separated and removed for example, by distillation, from a free compound of optically active 2,2-dimethylcyclopropanecarboxylic acid.

The thus-obtained optically active 2,2-dimethylcyclopropanecarboxylic acid can further be purified, as required, by distillation or the like.

Meanwhile, as described above, when the resulting optically active 2,2-dimethylcyclopropanecarboxylic acid has a low optical purity, the optical purity can be improved by repeating the invention. That is, the formation of its ammonium salt is repeated to be able to further improve the optical purity.

Optically active 2,2-dimethylcyclopropanecarboxylic acid contained in the mother liquor obtained after separation of the resulting ammonium salt or in the crystal-separated mother liquor after recrystallization is recovered by a known method, and racemized, as required, by a known method. Thus, the process of the invention can be applied thereto again.

As stated above, the ammonium salt of optically active 2,2-dimethylcyclopropanecarboxylic acid can also be formed by reacting the racemic modification of 2,2-dimethylcyclopropanecarboxylic acid with the optically inactive amine. In this case, in the formation of the ammonium salt, specifically the ammonium salt can easily be obtained by reacting optically active 2,2-dimethylcyclopropanecarboxylic acid with the optically inactive amine and then using (reacting), as a seed crystal, a desired ammonium salt of optically active 2,2-dimethylcyclopropanecarboxylic acid or an ammonium salt of optically active 2,2-dimethylcyclopropanecarboxylic acid having a high optical purity (for example, an ammonium salt of optically active (S)-(+)-2,2-dimethylcyclopropanecarboxylic acid when a desired compound is optically active (S)-(+)-2,2-dimethylcyclopropanecarboxylic acid). The thus-obtained optically active 2,2-dimethylcyclopropanecarboxylic acid (or its ammonium salt) is, in many cases, low in optical purity. However, the optical purity can further be improved by repeating the formation of its ammonium salt again as described above.

With respect to a method for producing the seed crystal, the desired seed crystal can easily be produced without special difficulty by dissolving a high-purity ammonium salt of optically active 2,2-dimethylcyclopropanecarboxylic acid obtained separately by an ordinary method in an appropriate solvent to precipitate the same.

When the ammonium salt is formed in the solvent and the resulting salt is separated by precipitation, crystallization or the like, especially when the ammonium salt is formed from the racemic modification as described above, the optical purity is low in many cases. Accordingly, the optical purity can be increased by subjecting the salt to the invention again or by recrystallization. The solvent used in this recrystallization is selected from among preferable solvents used in the formation of the ammonium salt, examples thereof including organic solvents such as ethyl acetate, isobutyl acetate, butyl acetate, toluene, methylene chloride, chloroform and an alcohol having from 1 to 4 carbon atoms, water and mixed solvents thereof. The recrystallization can be performed using the same.

The optically active substance formed by the process of the invention has quite a high optical purity, and can therefore be used in various intermediates. Further, considering that the formation can be performed by an easy operation using the optically inactive amine which is in general easily procured and less costly and the yield is good, the invention is quite useful as an industrial process.

Invention Method for Optical Purification of Optically Active 2,2-dimethylcyclopropanecarboxylic acid The invention method for optical purification of optically active 2,2-dimethylcyclopropanecarboxylic acid is a method in which an optical isomer mixture of 2,2-dimethylcyclopropanecarboxylic acid is reacted with an optically inactive amine to form an ammonium salt of optically active 2,2-dimethylcyclopropanecarboxylic acid, with the result that optically active 2,2-dimethylcyclopropanecarboxylic acid is separated from other optical isomers. For example, an ammonium salt of optically active (S)-(+)-2,2-dimethylcyclopropanecarboxylic acid is formed, so that the S-isomer can be separated from an R-isomer. The optical purity can further be improved by repeating again the formation of the ammonium salt used in the invention. This invention method per se can easily be performed by referring to the contents of the invention process for producing optically active 2,2-dimethylcyclopropanecarboxylic acid.

Invention Process for Producing a Free Compound of Optically Active 2,2-dimethylcyclopropanecarboxylic acid)

The invention process for producing a free compound of optically active 2,2-dimethylcyclopropanecarboxylic acid is a process which comprises subjecting optically active 2,2-dimethylcyclopropanecarboxylic acid in the form of an ammonium salt with an optically inactive amine, for example, an ammonium salt of optically active (S)-(+)-2,2-dimethyl-cyclopropanecarboxylic acid to a desalting step, namely a step of converting a salt to a free compound to form its free compound. This process can also be performed easily by referring to the contents described on the desalting step, namely the step of converting a salt to a free compound in the invention process for producing optically active 2,2-dimethylcyclopropanecarboxylic acid.

Invention Ammonium Salt

The invention ammonium salt is an addition salt of optically active 2, 2-dimethylcyclopropanecarboxylic acid and the optically inactive amine as described above.

The optical resolution agent used in the invention is obtained by using the optically inactive amine as an active ingredient, and the practicing method and the like are as described earlier.

PREFERRED EMBODIMENTS

The invention is illustrated specifically below by referring to Examples. However, the invention is not limited at all by these Examples. Incidentally, the contents of the concentrated residues were all estimated by $^1$H-NMR (CDCl$_3$)

Example 1

5 ml of ethyl acetate was added to 3.0 g (86.6% e.e., 26 mmol) of (S)-(+)-2,2-dimethylcyclopropanecarboxylic acid, and 2.6 g (26 mmol) of cyclohexylamine was added at 70° C. Crystals were then precipitated. Further, 55 ml of ethyl acetate and 24 ml of methanol (MeOH) were added thereto, and the mixture was heated to 80° C. or more with stirring to form a homogeneous solution. The solution was then cooled to 20° C. After the solution was stirred overnight, the precipitated crystals were filtered to obtain 1.6 g of cotton-like white crystals. 40 ml of water and 7 ml of 6M-HCl were added to the crystals to dissolve the crystals therein (adjust pH to 1 or less). The resulting solution was extracted three times with 50 ml of ethyl acetate, and separated into layers. The combined ethyl acetate layer was washed with 40 ml of water. Thereafter, the ethyl acetate layer was dried with anhydrous sodium sulfate, and then concentrated under reduced pressure to obtain 1.3 g of (S)-(+)-2,2-dimethylcyclopropanecarboxylic acid as a residue (content 72%, yield 30%). This was analyzed by gas chromatography (GC) using an optically active column (CP-Chirasil DEX CB manufactured by ChromPack, 0.25 mm×25 m df=0.25 mm), and the optical purity was 99.0% e.e.

Example 2

5 ml of ethyl acetate was added to 3.0 g (86.6% e.e., 26 mmol) of (S)-(+)-2,2-dimethylcyclopropanecarboxylic acid, and 3.5 g (26 mmol) of benzylamine was added at 50° C. Crystals were then precipitated. Further, 40 ml of ethyl acetate was added thereto, and the mixture was heated to 75° C. to form a homogeneous solution. The solution was then allowed to cool to 20° C., and stirred overnight at 20° C. The crystallized slurry was filtered to obtain 5 g of cotton-like crystals. 50 ml of water and 10 ml of 6M-HCl were added to the crystals to dissolve the crystals therein (adjust pH to 1 or less). The resulting solution was extracted three times with 100 ml of ethyl acetate, and separated into layers. The combined ethyl acetate layer was washed with 100 ml of water. Thereafter, the ethyl acetate layer was dried with anhydrous sodium sulfate, and concentrated under reduced pressure to obtain 2.4 g of (S)-(+)-2,2-dimethylcyclopropanecarboxylic acid as a residue (content 87%, yield 68%). The optical purity was 94.3% e.e. (analyzed by GC in the foregoing manner).

Example 3

5 ml of ethyl acetate was added to 3.0 g (86.6% e.e., 26 mmol) of (S)-(+)-2,2-dimethylcyclopropanecarboxylic acid, and 2.7 g (26 mmol) of diisopropylamine was added at room temperature. Crystals were then precipitated. Further, 5 ml of ethyl acetate was added thereto, and the mixture was heated to 70° C. to form a homogeneous solution. The solution was then allowed to cool to 20° C., and stirred overnight at 20° C. The precipitated crystals were filtered to obtain 4.4 g of the crystals. 40 ml of water and 20 ml of 6M-HCl were added to the crystals to dissolve the crystals therein (adjust pH to 1 or less). The resulting solution was extracted three times with 100 ml of ethyl acetate, and separated into layers. The combined ethyl acetate layer was then washed with 100 ml of water. The ethyl acetate layer was dried with anhydrous sodium sulfate, and concentrated under reduced pressure to obtain 2.7 g of (S)-(+)-2,2-dimethylcyclopropanecarboxylic acid as a residue (content 91%, yield 81%). The optical purity was 96.2% e.e. (analyzed by GC in the foregoing manner).

Example 4

10 ml of an ethyl acetate-methanol solution (8:2 v/v) was added to 3.0 g (86.6% e.e., 26 mmol) of (S)-(+)-2,2-dimethylcyclopropanecarboxylic acid, and 1.9 g (26 mmol) of t-butylamine was added thereto. Crystals were then precipitated. Further, 170 ml of an ethyl acetate-methanol solution (8:2 v/v) was added thereto, and the mixture was heated to 70° C. to form a homogeneous solution. When the solution was allowed to cool, crystals were precipitated at 48° C. The crystals were allowed as such to cool to 20° C., and stirred overnight at 20° C. Thereafter, the slurry was filtered to obtain 3.6 g of crystals. 40 ml of water and 15 ml of 6M-HCl were added to the crystals to dissolve the crystals therein (adjust pH to 1 or less). The solution was extracted three times with 100 ml of ethyl acetate, and then separated into layers. The combined ethyl acetate layer was washed with 100 ml of water. The ethyl acetate layer was further dried with anhydrous sodium sulfate, and concentrated under reduced pressure to obtain 2.6 g of (S)-(+)-2,2-dimethylcyclopropanecarboxylic acid as a residue (content 81%, yield 71%). The optical purity was 99.1% e.e. (analyzed by GC in the foregoing manner).

Example 5

20 ml of 2-propanol was added to 3.0 g (86.6% e.e., 26 mmol) of (S)-(+)-2,2-dimethylcyclopropanecarboxylic acid, and 1.9 g (26 mmol) of t-butylamine was added thereto. Crystals were then precipitated. Further, 85 ml of 2-propanol was added thereto, and the mixture was heated to 80° C. to form a homogeneous solution. When the solution was then allowed to cool, crystals were precipitated at 47° C. The crystals were allowed as such to cool to 20° C., and stirred overnight at 20° C. Thereafter, the slurry was filtered to obtain 3.4 g of crystals. The crystals were dissolved with 100 ml of water, and 10 ml of 6M-HCl was dissolved (adjust pH to 1 or less). The solution was extracted three times with 100 ml of ethyl acetate, and separated into layers. The combined ethyl acetate layer was then washed with 100 ml of water. The ethyl acetate layer was further dried with anhydrous sodium sulfate, and concentrated under reduced pressure to obtain 2.3 g of (S)-(+)-2,2-dimethylcyclopropanecarboxylic acid as a residue (content 93.8%, yield 70.3%). The optical purity was 99.8% e.e. (analyzed by GC in the foregoing manner).

From the foregoing results, it is found that the process of the invention is quite easy and the product of the invention is excellent in optical purity.

ADVANTAGE OF THE INVENTION

According to the invention, the desired compound can easily be produced by efficiently separating and purifying optically active 2,2-dimethylcyclopropanecarboxylic acid which is important as an intermediate of agricultural chemicals, medications and the like from 2,2-dimethylcyclopropanecarboxlyic acid including its optical isomer mixture (a racemic modification or an optically impure substance).

Since a desired optically active substance can be produced easily and conveniently using an optically inactive amine as an optical resolution agent which can provide excellent yield and optical purity and be procured easily, the invention is industrially quite useful.

The invention also provides the optical resolution agent (optically inactive amine) used in the separation and purification, and the intermediate (the ammonium salt of optically active 2,2-dimethylcyclopropanecarboxylic acid and the optically inactive amine, especially preferably the ammonium salt of (S)-(+)-2,2-dimethylcyclopropanecarboxylic acid and the optically inactive amine, or the like).

What is claimed is:

1. A process for producing optically active 2,2-dimethylcyclopropanecarboxylic acid, comprising:
    reacting an optical isomer mixture of 2,2-dimethylcyclopropanecarboxylic acid with an optically inactive amine to form a reactant solution comprising an ammonium salt of optically active (S)-2,2-dimethylcyclopropanecarboxylic acid wherein the ratio of the (S)-(+)-2,2-dimethylcyclopropanecarboxylic acid to another isomer of 2,2-dimethylcyclopropanecarboxylic acid is 1:1 or greater; and
    precipitating or crystallizing the ammonium salt of optically active (S)-2,2-dimethylcyclopropanecarboxylic acid from the reactant solution;
    wherein any optically active (R)-2,2-dimethylcyclopropane carboxylic acid remains in solution.

2. The process according to claim 1, wherein the optical isomer mixture is a racemic modification of 2,2-dimethylcyclopropanecarboxylic acid.

3. The process according to claim 1, wherein the optically inactive amine is a primary to tertiary amine represented by the following general formula (1),

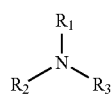

(1)

wherein $R_1$, $R_2$ and $R_3$ are independent, and each represents a saturated or unsaturated, linear or branched hydrocarbon group with from 1 to 8 carbon atoms which is optionally substituted with an alicyclic or aromatic substituent; a heterocyclic hydrocarbon group containing an oxygen atom, a nitrogen atom, or both, and which optionally is substituted with a saturated or unsaturated, linear or branched hydrocarbon substituent group having from 1 to 8 carbon atoms; an alicyclic hydrocarbon group with from 3 to 8 carbon atoms; an aromatic hydrocarbon group which is optionally substituted with a saturated or unsaturated, linear or branched hydrocarbon substituent group having from 1 to 8 carbon atoms; or a hydrogen atom.

4. The process according to claim 1, wherein the optically inactive amine is selected from the group consisting of t-butylamine, cyclohexylamine, diisopropylamine, dicyclohexylamine, benzylamine, and mixtures thereof.

5. The process according to claim 1, further comprising subjecting the ammonium salt of optically active (S)-2,2-dimethylcyclopropanecarboxylic acid to a desalting step to form a free compound of the optically active (S)-2,2-dimethylcyclopropanecarboxylic acid.

6. The process according to claim 1, wherein the optically active 2,2-dimethylcyclopropanecarboxylic acid is in the form of an ammonium salt.

7. The process according to claim 2, wherein the optically inactive amine is a primary to tertiary amine represented by the following general formula (1),

(1)

wherein $R_1$, $R_2$ and $R_3$ are independent, and each represents a saturated or unsaturated, linear or branched hydrocarbon group with from 1 to 8 carbon atoms optionally substituted with an alicyclic or aromatic substituent; a heterocyclic hydrocarbon group having an oxygen atom, a nitrogen atom, or both, and which is optionally substituted with a saturated or unsaturated, linear or branched hydrocarbon substituent group having from 1 to 8 carbon atoms; an alicyclic hydrocarbon group with from 3 to 8 carbon atoms; an aromatic hydrocarbon group which is optionally substituted with a saturated or unsaturated, linear or branched hydrocarbon substituent group having from 1 to 8 carbon atoms; or a hydrogen atom.

8. The process according to claim 3, wherein the optically inactive amine is at least one of t-butylamine, cyclohexylamine, diisopropylamine, dicyclohexylamine and benzylamine.

9. The process according to claim 2, further comprising subjecting the ammonium salt of optically active (S)-2,2-dimethylcyclopropanecarboxylic acid to a desalting step to form a free compound of the optically active (S)-2,2-dimethylcyclopropanecarboxylic acid.

10. The process according to claim 3, further comprising subjecting the ammonium salt of optically active (S)-2,2-dimethylcyclopropanecarboxylic acid to a desalting step to form a free compound of the optically active (S)-2,2-dimethylcyclopropanecarboxylic acid.

* * * * *